United States Patent
Adam et al.

[11] Patent Number: 5,958,931
[45] Date of Patent: Sep. 28, 1999

[54] PHENYL-SUBSTITUTED 5H-THIAZOLO[3,2-A]PYRIMIDINE DERIVATIVE GLUTAMATE RECEPTOR ANTAGONISTS

[75] Inventors: Geo Adam, Schopfheim; Sabine Kolczewski, Lörrach, both of Germany; Vincent Mutel, Mulhouse, France; Jürgen Wichmann, Steinen; Thomas Johannes Woltering, Weil am Rhein, both of Germany

[73] Assignee: Hoffmann-La Roche Inc., Nutley, N.J.

[21] Appl. No.: 09/115,191

[22] Filed: Jul. 14, 1998

[30] Foreign Application Priority Data

Jul. 18, 1997 [EP] European Pat. Off. ............ 97112324

[51] Int. Cl.⁶ ........................ A61K 31/505; C07D 513/04
[52] U.S. Cl. ............................................ 514/258; 544/278
[58] Field of Search ........................... 514/258; 544/278, 544/282

[56] References Cited

U.S. PATENT DOCUMENTS 3,660,418  5/1972  Manning et al. .................. 548/154

FOREIGN PATENT DOCUMENTS

20380/92   1/1993   Australia.
696 577    2/1996   European Pat. Off..
807 621   11/1997   European Pat. Off..
WO 98/06724 8/1997  WIPO.

OTHER PUBLICATIONS

Sudan et al., J. Indian Chem. Soc. 73:431–434 (Aug. 1996).
Ertan et al., Arznem. Forsch./Drug Research 41(II):725–727 (1991).
Sherif et al., Tetrahedron 49:9561–9572 (1993).
Bozsing et al., Eur. J. Med. Chem. 31:663–668 (1996).
CA 118:59669, 1992.
British Journal of Pharmacology 123:497–504 (1998).

*Primary Examiner*—John M. Ford
*Assistant Examiner*—Ann M. Kessinger
*Attorney, Agent, or Firm*—George W. Johnston; Dennis P. Tramaloni; Joseph P. Kirk, Jr.

[57] ABSTRACT

The invention is concerned with compounds of the general formula

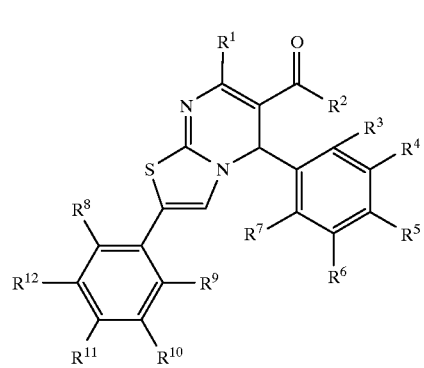

wherein
  $R^1$ is hydrogen, lower alkyl, phenyl or benzyl,
  $R^2$ is lower alkyl, lower alkoxy, —O(CH$_2$)$_n$N(R$^{13}$)(R$^{14}$), —(CH$_2$)$_n$N(R$^{13}$)(R$^{14}$) or —N(R$^{15}$)(CH$_2$)$_n$N(R$^{13}$)(R$^{14}$),
  $R^3$–$R^{12}$ are hydrogen, halogen, trifluoromethyl, lower alkyl, cycloalkyl, lower alkoxy, hydroxy, nitro, cyano, —N(R$^{13}$)$_2$, phenyl, phenyloxy, benzyl or benzyloxy, or
  $R^6$ and $R^7$ together are a benzene ring,
  $R^{13}$–$R^{15}$ are hydrogen, lower alkyl or cycloalkyl and
  n is 1–5,
as well as their pharmaceutically acceptable salts.

21 Claims, No Drawings

PHENYL-SUBSTITUTED 5H-THIAZOLO[3,2-A]PYRIMIDINE DERIVATIVE GLUTAMATE RECEPTOR ANTAGONISTS

BACKGROUND OF THE INVENTION

In the central nervous system (CNS) the transmission of stimuli takes place by the interaction of a neurotransmitter, released by a neuron, with a neuroreceptor.

L-glutamic acid (glutamate), the most commonly occurring neurotransmitter in the CNS, plays a critical role in a large number of physiological processes. The glutamate-dependent stimulus receptors are divided into two main groups. The first main group forms ligand-controlled ion channels. The second main group forms G-protein-coupled receptors, and includes the metabotropic glutamate receptors (mGluR).

At present eight different members of these mGluR are known and of these some even have sub-types. On the basis of structural parameters, their different influences on the synthesis of secondary metabolites and their different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Metabotropic glutamate receptors belonging to the second group can be used for the treatment or prevention of diseases and conditions related to the functioning of the mGluR. These include acute and/or chronic neurological disorders such as restricted brain function caused by bypass operations or transplants, poor blood supply to the brain, spinal cord injuries, head injuries, hypoxia caused by pregnancy, cardiac arrest and hypoglycaemia. Other treatable indications in this connection are Alzheimer's disease, Huntington's chorea, amyotrophic lateral sclerosis (ALS), dementia caused by AIDS, eye injuries, retinopathy, cognitive disorders, idiopathic parkinsonism or parkinsonism caused by medicaments as well as conditions which lead to glutamate-deficiency conditions, such as muscle spasms, convulsions, migraine, urinary incontinence, nicotine addiction, psychoses, opiate addiction, anxiety, vomiting, chronic pain, dyskinesia, depressions and pains (see for example EP 807 621 and EP 696 577).

SUMMARY OF THE INVENTION

The present invention is concerned with 5H-thiazolo[3,2—a]pyrimidine derivatives of the general formula

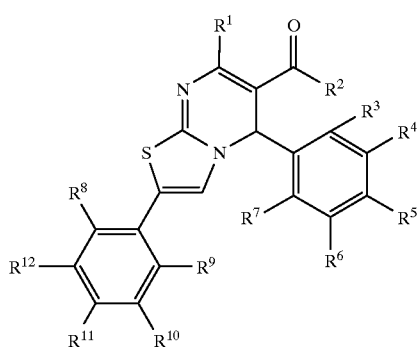

I wherein
$R^1$ is hydrogen, lower alkyl, phenyl or benzyl,
$R^2$ is lower alkyl, lower alkoxy, —O(CH$_2$)$_n$N(R$^{13}$)(R$^{14}$), —(CH$_2$)$_n$N(R$^{13}$)(R$^{14}$) or —N(R$^{15}$)(CH$_2$)$_n$N(R$^{13}$)(R$^{14}$),
$R^3$–$R^{12}$ are hydrogen, halogen, trifluoromethyl, lower alkyl, cyclo alkyl, lower alkoxy, hydroxy, nitro, cyano, —N(R$^{13}$)$_2$, phenyl, phenyloxy, benzyl or benzyloxy, or
$R^6$ and $R^7$ together are a benzene ring,
$R^{13}$–$R^{15}$ are hydrogen, lower alkyl or cycloalkyl and
n is 1–5,
as well as their pharmaceutically acceptable salts.

These compounds and their salts are novel and are distinguished by valuable therapeutic properties. Specifically it has been found that the compounds of general formula I are metabotropic glutamate receptor antagonists. These compounds are capable of high affinity binding to group II mGluR receptors. As antagonists, they can be used to treat diseases and conditions described above which result from excessive mGluR stimulation.

DETAILED DESCRIPTION OF THE INVENTION

Objects of the present invention are compounds of formula I and their pharmaceutically acceptable salts per se and as pharmaceutically active substances, their manufacture, medicaments based on a compound in accordance with the invention and their production as well as the use of the compounds in accordance with the invention in the control or prevention of illnesses of the aforementioned kind, and, respectively, for the production of corresponding medicaments.

Preferred compounds of formula I include compounds where $R^1$ is lower alkyl or benzyl; $R^2$ is lower alkyl, lower alkoxy, —O(CH$_2$)$_2$N(CH$_3$)$_2$, —O(CH$_2$)$_3$N(CH$_3$)$_2$, —NH(CH$_2$)$_2$N(CH$_3$)$_2$ or —(CH$_3$) (CH$_2$)$_2$N(CH$_3$)$_2$; $R^3$ is hydrogen, lower alkoxy, halogen or benzyloxy; $R^4$ is hydrogen or lower alkoxy; $R^5$ is hydrogen, halogen or lower alkoxy; $R^6$ is hydrogen; $R^7$ is hydrogen or lower alkoxy; or $R^6$ and $R^7$ together are a benzene ring; and $R^8$–$R^{12}$ are hydrogen or halogen. Especially preferred are such compounds where $R^1$ is methyl or ethyl or isopropyl; $R^2$ is —O(CH$_2$)$_2$N(CH$_3$)$_2$; $R^3$ is hydrogen, methoxy, chlorine or isopropoxy; $R^5$ is hydrogen or methoxy; $R^4$ $R^6$, and $R^7$ are hydrogen; and $R^8$–$R^{12}$ are hydrogen or chlorine. Examples of such compounds are:

2-dimethylamino-ethyl (RS)-2-(2,6-dichlorophenyl)-5-(4-methoxyphenyl)-7-methyl-5H-thiazolo [3,2-a] pyrimidine-6-carboxylate.

2-dimethylamino-ethyl (RS)-2-(2,6-dichlorophenyl)-5-(2-methoxyphenyl)-7-methyl-5H-thiazolo [3,2-a] pyrimidine-6-carboxylate.

2-dimethylamino-ethyl (RS)-2-(2,4-dichlorophenyl)-5-(2-methoxyphenyl)-7-methyl-5H-thiazolo [3,2-a] pyrimidine-6-carboxylate.

2-dimethylamino-ethyl (RS)-2-(2,6-dichlorophenyl)-5-(2-chlorophenyl)-7-methyl-5H-thiazolo [3,2-a]pyrimidine-6-carboxylate.

2-dimethylamino-ethyl (RS)-2-(2,6-dichlorophenyl)-5-(2-chlorophenyl)-7-methyl-5H-thiazolo [3,2-a]pyrimidine-6-carboxylate 2-dimethylamino-ethyl (RS)-2-(2,6-dichlorophenyl)-5-(2-methoxyphenyl)-7-ethyl-5H-thiazolo [3,2-a]pyrimidine-6-carboxylate.

2-dimethylamino-ethyl (RS)-2-(2,6-dichlorophenyl)-5-(2-isopropyloxyphenyl)-7-methyl-5H-thiazolo [3,2-a] pyrimidine-6-carboxylate.

2-dimethylamino-ethyl (RS)-2-(2,4-dichlorophenyl)-5-(2-methoxyphenyl)-7-ethyl-5H-thiazolo [3,2-a]pyrimidine-6-carboxylate.

Also preferred are compounds where $R^1$ is lower alkyl; $R^2$ is —O(CH$_2$)$_n$N(CH$_3$)$_2$, —NH(CH$_2$)$_n$N(CH$_3$)$_2$ or —N(CH$_3$)(CH$_2$)$_n$N(CH$_3$)$_2$; n is 1–3; $R^3$ is lower alkoxy; $R^4$–$R^6$ and $R^{10}$–$R^{12}$ are hydrogen; and $R^8$ and $R^9$ are halogen are contemplated. Especially preferred are such compounds where $R^1$ is methyl, ethyl, or isopropyl; $R^3$ is methoxy; ethoxy; or isopropoxy; and $R^8$ and $R^9$ are chlorine, in particular when $R^1$ is methyl and $R^3$ is methoxy.

This invention also includes compounds of formula I having any one or more of the preferred substituents described above, for example a compound where $R^1$ is lower alkyl, $R^2$ is lower alkyl, lower alkoxy, —O(CH$_2$)$_n$N(R$^{13}$)(R$^{14}$), —(CH$_2$)$_n$N(R$^{13}$)(R$^{14}$) or —N(R$^{15}$)(CH$_2$)$_n$N(R$^{13}$)(R$^{14}$),$R^3$–$R^{12}$ are hydrogen, halogen, trifluoromethyl, lower alkyl, cycloalkyl, lower alkoxy, hydroxy, nitro, cyano, —N(R$^{13}$)$_2$, phenyl, phenyloxy, benzyl or benzyloxy, or $R^6$ and $R^7$ together are a benzene ring, $R^{13}$–$R^{15}$ are hydrogen, lower alkyl or cycloalkyl and n is 1–5, or a compound where $R^1$ is lower alkyl, $R^2$ is O(CH$_2$)$_n$N(R$^{13}$)(R$^{14}$), —(CH$_2$)$_n$N(R$^{13}$)(R$^{14}$) or —N(R$^{15}$)(CH$_2$)$_n$N(R$^{13}$)(R$^{14}$), $R^3$–$R^{12}$ are hydrogen or halogen, $R^{13}$–$R^{15}$ are hydrogen, lower alkyl or cycloalkyl and n is 2–3. Other compounds of formula I having combinations of preferred substituents where any one or more of R1 through R15 are preferred substituents as described above, are contemplated herein.

Objects of the invention are, furthermore, the novel compounds of the formula

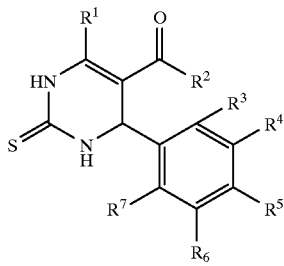

wherein $R^1$–$R^7$ have the significances given earlier, which are intermediates in the manufacture of the compounds of formula I.

The invention embraces all those stereoisomeric forms in addition to the racemates which may be obtained by conventional methods or as disclosed herein.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like and preferably straight-chain. The term "lower alkoxy" denotes a lower alkyl residue in the sense of the foregoing definition bonded via an oxygen atom. The term "cycloalkyl" denotes cyclic saturated hydrocarbon residues with 3–7 ring carbon atoms, such as, for example, cyclopropyl, cyclobutyl, cyclopentyl, cyclohexyl and the like. The term "halogen" embraces fluorine, chlorine, bromine and iodine.

The compounds of general formula I and their pharmaceutically acceptable salts can be manufactured by reacting a compound of the formula

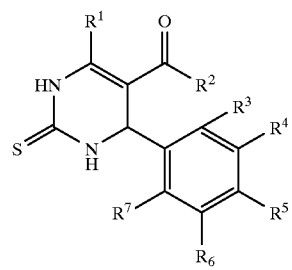

with an α-bromo-acetaldehyde of the formula

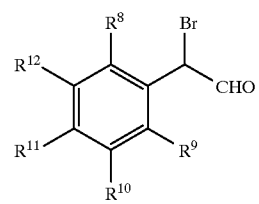

and, if desired, converting a functional group in a compound of formula I into another functional group by conventional methods and, if desired, converting a compound of formula I into a pharmaceutically acceptable salt.

In particular, nitro groups of compounds of formula I can be hydrogenated to amino groups or amino groups can be alkylated to lower alkylamino or di-lower-alkylamino groups or hydroxy groups can be alkylated.

In accordance with the invention an appropriately substituted α-bromoacetaldehyde of formula III, for example α-bromo-2,6-dichlorophenyl-acetaldehyde, is reacted with a suitable thioxopyrimidine of formula II, for example (RS)-1-[4-(4-methoxyphenyl)-6-methyl-2-thioxo-1,2,3,4-tetrahydro-pyrimidin-5-yl]ethanone. The reaction takes place at room temperature within 60–70 hours in an inert solvent, for example in tetrahydrofuran (THF), or in acetonitrile. After cooling the reaction mixture to about 0° C. the separated solid is heated with concentrated acetic acid for several hours and purified using known methods.

Nitro groups present can be hydrogenated to amino groups according to methods known per se. The hydrogenation is preferably effected with Raney-nickel at room temperature under normal pressure, where no chlorine is present in the molecule.

The alkylation of amino groups can be conveniently carried out as follows: A compound of general formula I which contains an amino group is, for example, dissolved in acetonitrile and treated with formaldehyde and NaBH$_3$CN. After adjustment to pH 6 with, for example, glacial acetic acid this procedure is repeated, with a methylamino compound of formula I being obtained after a reaction period of about 2 hours. Another method comprises treatment of a compound of formula I which contains an amino group with, for example, formic acid esters and subsequent hydrogenation in a BH$_3$-THF solution.

The alkylation of a hydroxy group can be carried out according to generally familiar methods. Dimethyl sulphate can be conveniently used as the alkylating agent for a methylation. This can be carried out by dissolving the compound to be alkylated in a suitable solvent, e.g. toluene, treating with dimethyl sulphate, tetrabutylammonium hydrogen sulphate and a sodium hydroxide solution and stirring intensively. The reaction conditions can be varied according to alkylating agent and, respectively, compound to be alkylated.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds.

The following Scheme gives an overview of the manufacture of the compounds of formula I starting from the compounds of formulae IV, V and VI. The intermediates of formula II are novel. The α-bromoacetyldehydes can be prepared according to U.S. Pat. No. 3,660,418 (incorporated by reference). The manufacture of representative compounds of formula I is described in detail in Examples 1–27.

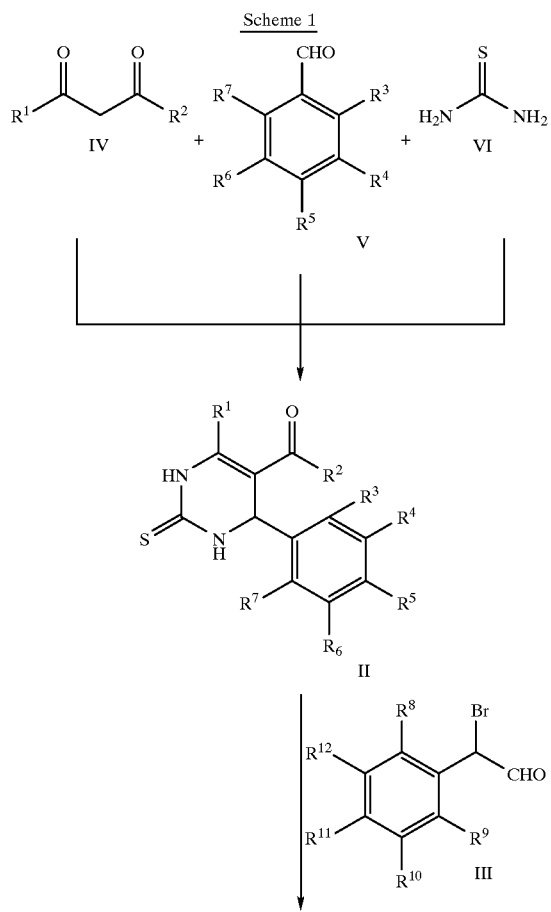

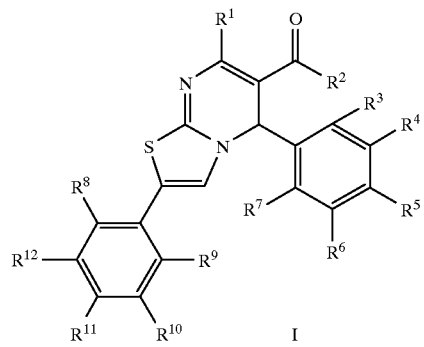

The substituents have the significances given earlier.

The compounds of formula I and their pharmaceutically acceptable salts are, as already mentioned above, metabotropic glutamate receptor antagonists and can be used for the treatment or prevention of acute and/or chronic neurological disorders, such as restricted brain function caused by bypass operations or transplants, poor blood supply to the brain, spinal cord injuries, head injuries, hypoxia caused by pregnancy, cardiac arrest and hypoglycaemia. Other treatable indications are Alzheimer's disease, Huntington's chorea, ALS, dementia caused by AIDS, eye injuries, retinopathy, cognitive illnesses, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, chronic pain, dyskinesia, depressions and pains.

The pharmaceutical activity of compounds of formula I is established by binding assays which determine that a compound binds to a group II mGluR. Binding assays are known to a skilled practitioner. One such assay, provided below, is also described for example in British Journal of Pharmacology, 123:497–504 (1998). By means of this assay, the binding of the compounds of formula I in accordance with the invention to group II metabotropic glutamate receptors is determined in vitro. The preparations were investigated in accordance with the test given hereinafter.

The GTP $\gamma^{35}$S test was used to determine the affinity of a compound to the group II mGluR. These were stimulated with 10 $\mu$M 1S,3R-ACPD.

The Ki values of the compounds tested are given. The Ki value is defined by the following formula:

$$K_i = \frac{IC_{50}}{1 + \frac{[L]}{EC_{50}}}$$

in which the $IC_{50}$ values are those concentrations of the compounds tested in $\mu$M by which 50% of the effect of 1S,3R-ACPD are antagonised. [L] is the concentration of IS,3R-ACPD and the $EC_{50}$ value is the concentration of 1S,3R-ACPD in $\mu$M which brings about 50% stimulation.

The compounds described in Examples 1–27 have activities of Ki=1–20 $\mu$M.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

Thus part of this invention is a pharmaceutical composition which comprises a compound o formula I, in particular a preferred compound as described above, and a pharmaceutically acceptable carrier. The compounds of formula I and pharmaceutically acceptable salts thereof can be processed with pharmaceutically acceptable carriers, e.g. inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

Accordingly, also part of this invention is a method of treating acute and/or chronic neurological disorders such as restricted brain function caused by bypass operations or transplants, poor blood supply to the brain, spinal cord injuries, head injuries, hypoxia cause by pregnancy, cardiac arrest, hypoglycaemia, Alzheimer's disease, Huntington's chorea, ALS, dementia caused by AIDS, eye injuries, retinopathy, cognitive disorders, idiopathic parkinsonism or parkinsonism caused by medicaments as well as conditions which lead to glutamate deficiency functions, such as e.g. muscle spasms, convulsions, migraine, urinary incontinence, nicotine addiction, psychoses, opiate addiction, anxiety, vomiting, chronic pain, dyskinesia and depressions which comprises administering to a patient having any of the above conditions an amount of the pharmaceutical composition of this invention effective to treat or prevent said condition.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

The examples which follow are provided by way of illustration and do not limit the invention in any way.

EXAMPLE 1

(RS)-1-[2-(2,6- Dichlorophenyl)-5-(4-methoxyphenyl)-7-methyl-5H-thiazolo[3,2-a]- pyrimidin-6-yl]ethanone a) A solution of 12.1 ml (0.1 mol) of 4-methoxybenzaldehyde, 10.3 ml (0.1 mol) of acetylacetone and 9.13 g (0.12 mol) of thiourea in 30 ml of ethanol was treated with 10 drops of conc. hydrochloric acid and boiled under reflux while stirring for 4 h. The reaction mixture was concentrated and the residue was purified by column chromatography on silica gel (dichloromethane-methanol 98:2). Subsequent crystallization from ethanol gave 6.2 g (22%) of (RS)-1-[4-(4-methoxyphenyl)-6-methyl-2-thioxo-1,2,3,4-tetrahydro-pyrimidin-5-yl]ethanone as a red-brown solid with m.p. 175° C.

b) A mixture of 1.9 g (7.09 mmol) of α-bromo-2,6-dichlorophenyl-acetaldehyde and 1.78 g (6.45 mmol) of (RS)-1-[4-(4-methoxyphenyl)-6-methyl-2-thioxo-1,2,3,4-tetrahydro-pyrimidin-5-yl]ethanone in 50 ml of tetra- hydrofuran was stirred at RT for 65 h. Subsequently, the mixture was cooled to 0° C. and the precipitated solid was filtered off, dissolved in 75 ml of conc. acetic acid and heated at reflux while stirring for 8 h. The reaction mixture was concentrated and the residue was purified by column chromatography on silica gel (dichloromethane/methanol 95:5). There were obtained 1.95 g (68%) of (RS)-1-[2-(2,6-dichlorophenyl)-5-(4-methoxyphenyl)-7-methyl-5H-thiazolo[3,2-a]pyrimidin-6-yl]ethanone as a yellow foam.

c) 1.95 g (4.38 mmol) of (RS)-1-[2-(2,6-dichlorophenyl)-5-(4-methoxyphenyl)-7-methyl-5H-thiazolo[3,2-a]pyrimidin-6-yl]ethanone were dissolved in 20 ml of methanolic hydrochloric acid solution (2.6N) while stirring and treated with 100 ml of diethyl ether. After 1 h the crystals were filtered off. There were obtained 1.54 g (73%) of (RS)-1-[2-(2,6-dichlorophenyl)-5-(4-methoxyphenyl)-7-methyl-5H-thiazolo[3,2-a]pyrimidin-6-yl]ethanone hydrochloride as a beige solid with m.p. 165° C.

EXAMPLE 2

(RS)-1-[2-(2,6-Dichlorophenyl)-5-(2-methoxyphenyl)-7-methyl-5H-thiazolo[3,2-a]pyrimidin-6-yl]ethanone Analogously to Example 1a–c, starting from 2-methoxybenzaldehyde, thiourea, acetylacetone and α-bromo-2,6-dichlorophenyl-acetaldehyde there was obtained, after salt formation and crystallization, (RS)-1-[2-(2,6-dichlorophenyl)-5-(2-methoxyphenyl)-7-methyl-5H-thiazolo[3,2-a]pyrimidin-6-yl]ethanone hydrobromide as a white solid with m.p. 290° C.

EXAMPLE 3

Ethyl (RS)-2-(2,6-dichlorophenyl)-5-(2-methoxyphenyl)-7-methyl-5H-thiazolo[3,2-a]pyrimidine-6-carboxylate a) A mixture of 2.0 g (7.5 mmol) of α-bromo-2,6-dichlorophenyl-acetaldehyde and 2.08 g (6.8 mmol) of ethyl (RS)-4-(2-methoxyphenyl)-6-methyl-2-thioxo-1,2,3,4-tetrahydro-pyrimidine-5-carboxylate in 40 ml of tetrahydrofuran was stirred at RT for 17 h. Subsequently, the mixture was cooled to 0° C. and the precipitated solid was filtered off, dissolved in 75 ml of conc. acetic acid and heated at reflux while stirring for 24 h. The reaction mixture was concentrated and the residue was purified by column chromatography on silica gel (ethyl acetate). There were obtained 1.82 g (51%) of ethyl (RS)-2-(2,6-dichlorophenyl)-5-(2-methoxyphenyl)-7-methyl-5H-thiazolo[3,2-a]pyrimidine-6-carboxylate as a yellow foam.

b) 1.82 g (3.83 mmol) of ethyl (RS)-2-(2,6-dichlorophenyl)-5-(2-methoxyphenyl)-7-methyl-5H-thiazolo[3,2-a]pyrimidine-6-carboxylate were dissolved in 20 ml of methanolic hydrochloric solution (2.6N) while stirring and treated with 100 ml of diethyl ether. After 15 h. the crystals were filtered off. There were obtained 1.55 g (79%) of ethyl (RS)-2-(2,6-dichlorophenyl)-5-(4-methoxyphenyl)-7-methyl-5H-thiazolo[3,2-a]pyrimidine-6-carboxylate hydrochloride as a light yellow solid with m.p. 233° C.

EXAMPLE 4

(RS)-2-(2,6-Dichlorophenyl)-5-(4-methoxyphenyl)-7-methyl-5H-thiazolo[3,2-a]pyrimidin-6-carboxylate Analogously to Example 3a–b, starting from ethyl (RS)-4-(4-methoxyphenyl)-6-methyl-2-thioxo-1,2,3,4-tetrahydro-pyrimidine-5-carboxylate and α-bromo-2,6-dichlorophenyl-acetaldehyde there was obtained, after salt formation and crystallization, ethyl (RS)-2-(2,6-dichlorophenyl)-5-(4-methoxyphenyl)-7-methyl-5H-thiazolo[3,2-a]pyrimidine-6-carboxylate hydrochloride as a white solid with m.p. 201° C.

EXAMPLE 5

2-Dimethylamino-ethyl (RS)-2-(2,6-dichlorophenyl)-5-(4-methoxyphenyl)-7-methyl-5H-thiazolo[3,2-a]pyrimidine-6-carboxylate a) A solution of 3.0 g (17.3 mmol) of 2-dimethylaminoethyl 3-oxo-butanoate, 2.1 ml (17.3 mmol) of 4-methoxybenzaldehyde and 1.58 g (20.8 mmol) of thiourea in 15 ml of conc. acetic acid was heated under reflux for 4 h. The reaction mixture was concentrated and the residue was purified by column chromatography on silica gel (dichloromethane/- methanol/- ammonium hydroxide solution 8:1:0.1). There were obtained 2.76 g (46%) of 2-dimethyl-amino-ethyl (RS)-4-(4-methoxyphenyl)-6-methyl-2-thioxo-1,2,3,4-tetrahydro-pyrimidine-5-carboxylate as a light yellow solid with m.p. 80° C.

b) 0.9 g (2.6 mmol) of 2-dimethylamino-methyl (RS)-4-(4-methoxyphenyl)-6-methyl-2-thioxo-1,2,3,4-tetrahydro-pyrimidine-5-carboxylate was dissolved in 10 ml of methanolic hydrochloric acid solution and concentrated. The hydrochloride obtained and 0.77 g (2.86 mmol) of α-bromo-2,6-dichlorophenyl-acetaldehyde dissolved in 50 ml of acetonitrile were boiled under reflux while stirring for 16 h. The reaction mixture was concentrated and the residue was purified by column chromatography on silica gel (dichloromethane/methanol/- ammonium hydroxide solution 8:1:0.1). There was obtained 0.83 g (61%) of 2-dimethylamino-ethyl (RS)-2-(2,6-dichlorophenyl)-5-(4-methoxyphenyl)-7-methyl-5H-thiazolo[3,2-a]pyrimidine-6-carboxylate as a greenish foam.

c) 0.83 g (1.6 mmol) of 2-dimethylamino-ethyl (RS)-2-(2,6-dichlorophenyl)-5-(4-methoxyphenyl)-7-methyl-5H-thiazolo[3,2-a]pyrimidine-6-carboxylate was dissolved in 10 ml of methanolic hydrochloric acid solution (2.6N) while stirring and treated with 50 ml of diethyl ether. After 3 h. the crystals were filtered off. There was obtained 0.87 g (79%) of 2-dimethylamino-ethyl (RS)-2-(2,6-dichlorophenyl)-5-(4-methoxyphenyl)-7-methyl-5H-thiazolo[3,2-a]pyrimidine-6-carboxylate dihydrochloride as a beige solid with m.p.>240° C.

EXAMPLE 6

2-Dimethylamino-ethyl (RS)-2-(2,6-dichlorophenyl)-5-(2-methoxyphenyl)-7-methyl-5H-thiazolo[3,2-a]pyrimidine-6-carboxylate Analogously to Example 5a–c, starting from 2-methoxybenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-methoxyphenyl)-7-methyl-5H-thiazolo[3,2-a]pyrimidine-6-carboxylate dihydrobromide as a pale yellow solid with m.p. 237° C.

EXAMPLE 7

3-Dimethylamino-propyl (RS)-2-(2,6-dichlorophenyl)-5-(2-methoxyphenyl)-7-methyl-5H-thiazolo-[3,2-a]pyrimidine-6-carboxylate Analogously to Example 5a–c, starting from 2-methoxybenzaldehyde, 3-dimethylamino-propyl 3-oxo-butanoate, thiourea and α-bromo-2,6-dichlorophenyl-acetaldehyde there was obtained, after salt formation and crystallization, 3-dimethylamino-propyl (RS)-2-(2,6-dichlorophenyl)-5-(2-methoxyphenyl)-7-methyl-5H-thiazolo[3,2-a]pyrimidine-6-carboxylate dihydrochloride as a beige solid with m.p. 175° C. (dec.)

EXAMPLE 8

2-Dimethylamino-ethyl (RS)-2-(4-chlorophenyl)-5-(2-methoxyphenyl)-7-methyl-5H-thiazolo[3,2-a]-pyrimidine-6-carboxylate Analogously to Example 5a–c, starting from 2-methoxybenzaldehyde, 2-dimethylamino-ethyl 3-oxo-butanoate, thiourea and α-bromo-4-chlorophenyl-acetaldehyde there was obtained, after salt formation and crystallization, 2-dimethylamino-ethyl (RS)-2-(4-chlorophenyl)-5-(2-methoxyphenyl)-7-methyl-5H-thiazolo[3,2-a]pyrimidine-6-carboxylate dihydrochloride as a pale green solid with m.p. 178° C.

EXAMPLE 9

2-Dimethylamino-ethyl (RS)-2-(2,4-dichlorophenyl)-5-(2-methoxyphenyl)-7-methyl-5H-thiazolo[3,2-a]pyrimidine-6-carboxylate Analogously to Example 5a–c, starting from 2-methoxybenzaldehyde, 2-dimethylamino-ethyl 3-oxo-butanoate, thiourea and α-bromo-2,4-dichlorophenyl-acetaldehyde there was obtained, after salt formation and crystallization, 2-dimethylamino-ethyl (RS)-2-(2,4-dichlorophenyl)-5-(2-methoxyphenyl)-7-methyl-5H-thiazolo[3,2-a]pyrimidine-6-carboxylate dihydrochloride as a pale yellow solid with m.p. 191° C.

EXAMPLE 10

2-Dimethylamino-ethyl (RS)-2-(2,6-dichlorophenyl)-5-(3-methoxyphenyl)-7-methyl-5H-thiazolo[3,2-a]pyrimidine-6-carboxylate Analogously to Example 5a–c, starting from 3-methoxybenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(3-methoxyphenyl)-7-methyl-5H-thiazolo[3,2-a]pyrimidine-6carboxylate dihydrochloride as a beige solid with m.p. 155° C. (dec.).

EXAMPLE 11

2-Dimethylamino-ethyl (RS)-2-(2,6-dichlorophenyl)-5-(4-chlorophenyl)-7-methyl-5H-thiazolo[3,2-a]pyrimidine-6-carboxylate Analogously to Example 5a–c, starting from 4-chlorobenzaldehyde, 2-dimethylamino-ethyl 3-oxo-butanoate, thiourea and α-bromo-2,6-dichlorophenylacetaldehyde there was obtained, after salt formation and crystallization, 2-dimethylamino-ethyl (RS)-2-(2,6-dichlorophenyl)-5-(4-chlorophenyl)-7-methyl-5H-thiazolo[3,2-a]pyrimidine-6-carboxylate dihydrochloride as a beige solid with m.p. 190° C.

EXAMPLE 12
2-Dimethylamino-ethyl (RS)-2-(2,6-dichlorophenyl)-5-(2-chlorophenyl)-7-methyl-5H-thiazolo[3,2-a]pyrimidine-6-carboxylate Analogously to Example 5a–c, starting from 2-chlorobenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-chlorophenyl)-7-methyl-5H-thiazolo[3,2-a]pyrimidine-6-carboxylate dihydrochloride as a beige solid with m.p 169° C.

EXAMPLE 13
2-Dimethylamino-ethyl (RS)-2-(2,6-dichlorophenyl)-5-(2-methoxyphenyl)-7-iso-propyl-5H-thiazolo[3,2-a]pyrimidine-6-carboxylate Analogously to Example 5a–c, starting from 2-methoxybenzaldehyde, 2-dimethylamino-ethyl 4-methyl-3-oxo-pentanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-methoxyphenyl)-7-iso-propyl-5H-thiazolo[3,2-a]pyrimidine-6-carboxylate dihydrochloride as a beige solid with m.p. 165° C. (dec.).

EXAMPLE 14
2-Dimethylamino-ethyl (RS)-2-(2,6-dichlorophenyl)-5-(2-methoxyphenyl)-7-ethyl-5H-thiazolo[3,2-a]pyrimidine 6-carboxylate Analogously to Example 5a–c, starting from 2-methoxybenzaldehyde, 2-dimethylamino-ethyl 3-oxo-pentanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-methoxyphyenyl)-7-ethyl-5H-thiazolo[3,2-a]pyrimidine-6-carboxylate dihydrochloride as a beige solid with m.p. 167° C. (dec.).

EXAMPLE 15
2-Dimethylamino-ethyl (RS)-2-(2,6-dichlorophenyl)-5-(2-methoxyphenyl)-7-benzyl-5H-thiazolo[3,2-a]pyrimidine-6-carboxylate Analogously to Example 5a–c, starting from 2-methoxybenzaldehyde, 2-dimethylamino-ethyl 4-phenyl-3-oxo-butanate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-methoxyphenyl)-7-benzyl-5H-thiazolo[3,2-a]pyrimidine-6-carboxylate dihydrochloride as a beige solid with m.p. 170° C. (dec.).

EXAMPLE 16
(RS)-2-(2,6-Dichlorophenyl)-5-(2-methoxyphenyl)-7-benzyl-5H-thiazolo[3,2-a]pyrimidine-6-carboxylic acid N-(2-dimethylamino-ethyl)-amide Analogously to Example 5a–c, starting from 2-methoxybenzaldehyde, N-(2-dimethylamino-ethyl)-3-oxo-butanamide, thiourea and α-bromo-2,6-dichlorophenyl-acetaldehyde there was obtained, after salt formation and crystallization, (RS)-2-(2,6-dichlorophenyl)-5-(2-methoxyphenyl)-7-benzyl-5H-thiazolo [3,2-a]pyrimidine-6-carboxylic acid N-(2-dimethylamino-ethyl)-amide dihydrochloride as a beige solid with m.p. 232° C.

EXAMPLE 17
(RS)-2-(2,6-Dichlorophenyl)-5-(2-methoxyphenyl)-7-benzyl-5H-thiazolo[3,2-a]pyrimidine-6-carboxylic acid N-(2-dimethylamino-ethyl)-N-methyl-amide Analogously to Example 5a–c, starting from 2-methoxybenzaldehyde, N-(2-dimethylamino-ethyl)-N-methyl-3-oxo-butanimide, thiourea and α-bromo-2,6-dichlorophenyl-acetaldehyde there was obtained, after salt formation and crystallization, (RS)-2-(2,6-dichlorophenyl)-5-(2-methoxyphenyl)-7-benzyl-5H-thiazolo [3,2-a]pyrimidine-6-carboxylic acid N-(2-dimethylamino-ethyl)-N-methyl-amide dihydrochloride as a beige solid with m.p. 170° C. (dec.).

EXAMPLE 18
(RS)-2-(2,6-Dichlorophenyl)-5-(4-methoxyphenyl)-7-benzyl-5H-thiazolo[3,2-a]pyrimidine-6-carboxylic acid N-(2-dimethylamino-ethyl)-amide Analogously to Example 5a–c, starting from 4-methoxybenzaldehyde, N-(2-dimethylamino-ethyl)-3-oxo-butanamide, thiourea and α-bromo-2,6-dichlorophenyl-acetaldehyde there was obtained, after salt formation and crystallization, (RS)-2-(2,6-dichlorophenyl)-5-(4-methoxyphenyl)-7-benzyl-5H-thiazolo [3,2-a]pyrimidine-6-carboxylic acid N-(2-dimethylamino-ethyl)-amide dihydrochloride as a light yellow solid with m.p. 180° C. (dec.).

EXAMPLE 19
2-Dimethylamino-ethyl (RS)-2-(2,6-dichlorophenyl)-5-(2,3-dimethoxyphenyl)-7-methyl-5H-thiazolo [3,2-a]pyrimidine-6-carboxylate Analogously to Example 5a–c, starting from 2,3-dimethoxybenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2,3-dimethoxyphenyl)-7-methyl-5H-thiazolo [3,2-a]pyrimidine-6-carboxylate dihydrochloride as a light brown solid with m.p. 144° C.

EXAMPLE 20
2-Dimethylamino-ethyl (RS)-2-(2,6-dichlorophenyl)-5-(2,6-dimethoxyphenyl)-7-methyl-5H-thiazolo [3,2-a]pyrimidine-6-carboxylate Analogously to Example 5a–c, starting from 2,6-dimethoxybenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2,6-dimethoxyphenyl)-7-methyl-5H-thiazolo [3,2-a]pyrimidine-6-carboxylate dihydrochloride as a light green solid with m.p. 171° C. (dec.).

EXAMPLE 21
2-Dimethylamino-ethyl (RS)-2-(2,6-dichlorophenyl)-5-(2-fluorophenyl)-7-methyl-5H-thiazolo[3,2-a]pyrimidine-6-carboxylate Analogously to Example 5a–c, starting from 2-fluorobenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-fluorophenyl)-7-methyl-5H-thiazolo[3,2-a]pyrimidine-6-carboxylate dihydrochloride as a beige solid with m.p. 169° C. (dec.).

EXAMPLE 22

2-Dimethylamino-ethyl (RS)-2-(2,6-dichlorophenyl)-5-(2-methylphenyl)-7-methyl-5H-thiazolo[3,2-a]pyrimidine-6-carboxylate Analogously to Example 5a–c, starting from 2-methylbenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-methylphenyl)-7-methyl-5H-thiazolo[3,2-a]pyrimidine-6-carboxylate dihydrochloride as a beige solid with m.p. 157° C. (dec.).

EXAMPLE 23

2-Dimethylamino-ethyl (RS)-2-(2,6-dichlorophenyl)-5-(2-ethoxyphenyl)-7-methyl-5H-thiazolo[3,2-a]pyrimidine-6-carboxylate Analogously to Example 5a–c, starting from 2-ethoxybenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-ethoxyphenyl)-7-methyl-5H-thiazolo[3,2-a]pyrimidine-6-carboxylate dihydrochloride as a white solid with m.p. 188° C. (dec.).

EXAMPLE 24

2-Dimethylamino-ethyl (RS)-2-(2,6-dichlorophenyl)-5-(2-isopropyloxyphenyl)-7-methyl-5H-thiazolo [3,2-a] pyrimidine-6-carboxylate Analogously to Example 5a–c, starting from 2-iso-propyloxybenzaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-iso-propyloxyphenyl)-7-methyl-5H-thiazolo [3,2-a]pyrimidin-6-carboxylate dihydrochloride as a pale brown solid with m.p. 172° C. (dec.).

EXAMPLE 25

2-Dimethylamino-ethyl (RS)-2-(2,6-dichlorophenyl)-5-(2-methoxynaphthyl)-7-methyl-5H-thiazolo [3,2-a]pyrimidine-6-carboxylate Analogously to Example 5a–c, starting from 2-methoxynaphthaldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-methoxynaphthyl)-7-methyl-5H-thiazolo [3,2-a]pyrimidine-6-carboxylate dihydrochloride as a brown solid with m.p. 174° C. (dec.).

EXAMPLE 26

2-Dimethylamino-ethyl (RS)-2-(2,4-dichlorophenyl)-5-(2-methoxyphenyl)-7-ethyl-5H-thiazolo[3,2-a]pyrimidine-6-carboxylate Analogously to Example 5a–c, starting from 2-methoxybenzaldehyde, 2-dimethylamino-ethyl 3-oxo-pentanoate, thiourea and α-bromo-2,4-dichlorophenyl-acetaldehyde there was obtained, after salt formation and crystallization, 2-dimethylamino-ethyl (RS)-2-(2,4-dichlorophenyl)-5-(2-methoxyphenyl)-7-ethyl-5H-thiazolo [3,2-a]pyrimidine-6-carboxylate dihydrochloride as a yellow solid with m.p. 199° C. (dec.).

EXAMPLE 27

2-Dimethylamino-ethyl 12 (RS)-2-(2,6-dichlorophenyl)-5-(2-benzyloxyphenyl)-7-methyl-5H-thiazolo [3,2-a] pyrimidine-6-carboxylate Analogously to Example 5a–c, starting from 2-benzyloxybenzyldehyde, 2-dimethylamino-ethyl 3-oxo-butanoate, thiourea and α-bromo-2,6-dichlorophenyl-acetaldehyde there was obtained, after salt formation and crystallization, 2-dimethylamino-ethyl (RS)-2-(2,6-dichlorophenyl)-5-(2-benzyloxyphenyl)-7-methyl-5H-thiazolo [3,2-a]pyrimidine-6-carboxylate dihydrochloride as a light brown solid with m.p. 147° C. (dec.).

EXAMPLE A

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

We claim:
1. Compounds of the general formula

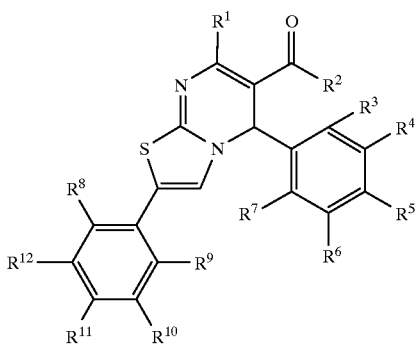

wherein
- $R^1$ is hydrogen, lower alkyl, phenyl or benzyl; $R^2$ is lower alkyl, $-O(CH_2)_nN(R^{13})(R^{14})$, $-(CH_2)_nN(R^{13})(R^{14})$ or $-N(R^{15})(CH_2)_nN(R^{13})(R^{14})$; $R^3$, $R^4$, $R^5$, $R^6$, $R^7$, $R^8$, $R^9$, $R^{10}$, $R^{11}$, and $R^{12}$ are each independently hydrogen, halogen, trifluoromethyl, lower alkyl, cycloalkyl, lower alkoxy, hydroxy, nitro, cyano, $-N(R^{13})_2$, phenyl, phenyloxy, benzyl or benzyloxy, or
- $R^6$ and $R^7$ together are a benzene ring; $R^{13}$, $R^{14}$, and $R^{15}$ are each independently hydrogen, lower alkyl or cycloalkyl; and n is 1–5, as well as their pharmaceutically acceptable salts.

2. Compounds of claim 1, wherein
$R^1$ is lower alkyl or benzyl; $R^2$ is lower alkyl, $-O(CH_2)_2N(CH_3)_2$, $-O(CH_2)_3N(CH_3)_2$, $-NH(CH_2)_2N(CH_3)_2$ or $-N(CH_3)(CH_2)_2N(CH_3)_2$; $R^3$ is hydrogen, lower alkoxy, halogen or benzyloxy; $R^4$ is hydrogen or lower alkoxy; $R^5$ is hydrogen, halogen or lower alkoxy; $R^6$ is hydrogen; $R^7$ is hydrogen or lower alkoxy; or $R^6$ and $R^7$ taken together are a benzene ring; and $R^8$, $R^9$, $R^{10}$, $R^{11}$, and $R^{12}$ are each independently hydrogen or halogen.

3. A compound of claim 1 wherein $R^1$ is lower alkyl; R2 is $-O(CH_2)_nN(CH_3)_2$, $-NH(CH_2)_nN(CH_3)_2$ or $-N(CH_3)(CH_2)_nN(CH_3)_2$; n is 1–3; $R^3$ is lower alkoxy; $R^4$, $R^5$, $R^6$, $R^{10}$, $R^{11}$, and $R^{12}$ are each hydrogen; and $R^8$ and R9 are halogen.

4. A compound of claim 3 wherein $R^1$ is methyl, ethyl, or isopropyl; $R^3$ is methoxy; ethoxy; or isopropoxy; and $R^8$ and $R^9$ are chlorine.

5. A compound of claim 4 wherein $R^1$ is methyl and $R^3$ is methoxy.

6. A compounds of claim 2 wherein $R^1$ is methyl or ethyl or isopropyl; $R^2$ is $-O(CH_2)_2N(CH_3)_2$; $R^3$ is hydrogen, methoxy, chlorine or isopropoxy; $R^5$ is hydrogen or methoxy; $R^4$ and $R^7$ are hydrogen; and $R^8$–$R^{12}$ are hydrogen or chlorine.

7. A compound of claim 6 which is 2-Dimethylaminoethyl (RS)-2-(2,6-dichlorophenyl)-5-(4-methoxypheny)-7-methyl-5H-thiazolo [3,2-a]pyrimidine-6-carboxylate.

8. A compound of claim 6 which is 2-dimethylaminoethyl (RS)-2-(2,6-dichlorophenyl)-5-(2-methoxyphenyl-7-methyl-5H-thiazolo [3,2-a]pyrimidine-6-carboxylate.

9. A compound of claim 6 which is 2-dimethylaminoethyl (RS)-2-(2,4-dichlorophenyl)-5-(2-methoxyphenyl)-7-methyl-5H-thiazolo [3,2-a]pyrimidine-6-carboxylate.

10. A compound of claim 6 which is 2-dimethylaminoethyl (RS)-2-(2,6-dichlorophenyl)-5-(2-chlorophenyl)-7-methyl-5H-thiazolo [3,2-a]pyrimidine-6-carboxylate.

11. A compound of claim 6 which is 2-dimethylaminoethyl (RS)-2-(2,6-dichlorophenyl)-5-(2-chlorophenyl)-7-methyl-5H-thiazolo [3,2-a]pyrimidine-6-carboxylate.

12. A compound of claim 6 which is 2-dimethylaminoethyl (RS)-2-(2,6-dichlorophenyl)-5-(2-methoxyphenyl)-7-ethyl-5H-thiazolo [3,2-a]pyrimidine-6-carboxylate.

13. A compound of claim 6 which is 2-dimethylaminoethyl (RS)-2-(2,6-dichlorophenyl)-5-(2-isopropyloxyphenyl)-7-methyl-5H-thiazolo [3,2-a] pyrimidine-6-carboxylate.

14. A compound of claim 6 which is 2-dimethylaminoethyl (RS)-2-(2,4-dichlorophenyl)-5-(2-methoxyphenyl)-7-ethyl-5H-thiazolo [3,2-a]pyrimidine-6-carboxylate.

15. A pharmaceutical composition which comprises a compound of claim 1 and a pharmaceutically acceptable carrier.

16. A process for the manufacture of compounds of claim 1-as well as of pharmaceutically acceptable salts thereof, which process comprises
reacting a compound of the formula

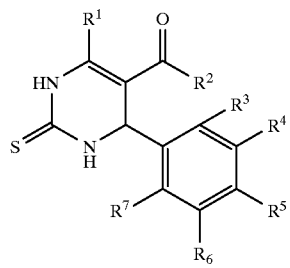

with an α-bromo-acetaldehyde of the formula

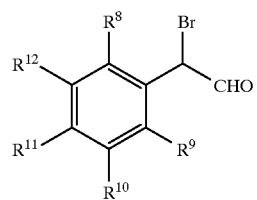

wherein $R^{1-R12}$ have the significance given in claim 1, and, if desired, converting a compound of formula I into a pharmaceutically acceptable salt.

17. Compounds of general formula

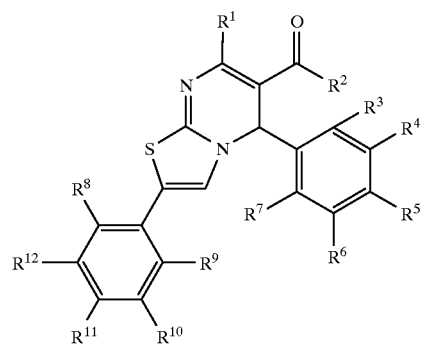

wherein $R^1$ is hydrogen, lower alkyl, phenyl or benzyl; $R^2$ is lower alkyl, —O(CH$_2$)$_n$N(R$^{13}$ R$^{14}$), -(CH$_2$) . . . are each independently trifluoromethyl, lower alkyl, cycloalkyl, lower alkoxy, hydroxy, nitro, cyano —N(R$^{13}$)$_2$, phenyl, phenyloxy, benzyl or benzyloxy, or $R^6$ and $R^7$ together are a benzene ring; $R^{13}$, $R^{14}$ and $R^{15}$ are each independently hydrogen, lower alkyl or cycloalkyl; and n is 1–5, prepared by the process of reacting a compound of the formula

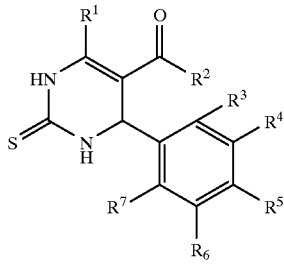

II with an α-bromo-acetaldehyde of the formula

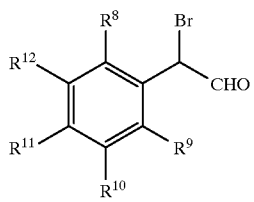

III wherein $R^1$–$R^{12}$ have the significance given above, and, if desired, converting a compound of formula I into a pharmaceutically acceptable salt.

18. Compounds of the general formula

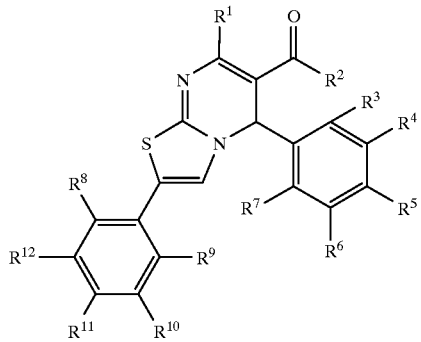

I wherein $R^1$ is hydrogen, lower alkyl, phenyl or benzyl; $R^2$ is ethoxy; $R^3$, $R^4$, $R^5$, $R^6$, $R^7$, $R^8$, $R^9$, $R^{10}$, $R^{11}$, and $R^{12}$ are each independently hydrogen, halogen, trifluoromethyl, lower alkyl, cycloalkyl, lower alkoxy, hydroxy, nitro, cyano, —N(R$^{13}$)$_2$, phenyl, phenyloxy, benzyl or benzyloxy, or $R^6$ and $R^7$ together are a benzene ring; $R^{13}$, $R^{14}$, and $R^{15}$ are each independently hydrogen, lower alkyl or cycloalkyl; as well as their pharmaceutically acceptable salts.

19. Compounds of claim 18, wherein $R^1$ is lower alkyl or benzyl; $R^2$ is ethoxy; $R^3$ is hydrogen, lower alkoxy, halogen or benzyloxy; $R^4$ is hydrogen or lower alkoxy; $R^5$ is hydrogen, halogen or lower alkoxy; $R^6$ is hydrogen; $R^7$ is hydrogen or lower alkoxy; or $R^6$ and $R^7$ taken together are a benzene ring; and $R^8$, $R^9$, $R^{10}$, $R^{11}$, and $R^{12}$ are each independently hydrogen or halogen.

20. Compounds of the general formula

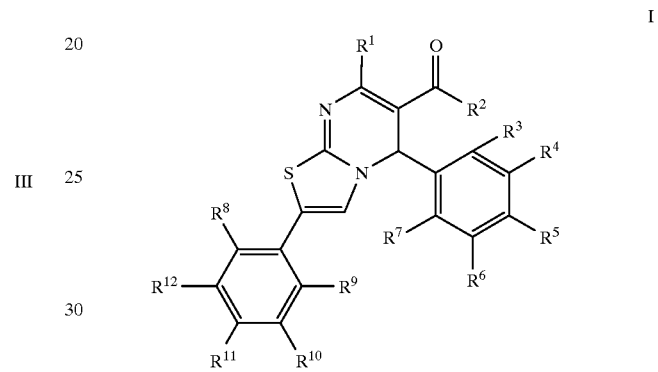

I wherein $R^1$ is hydrogen, lower alkyl, phenyl or benzyl; $R^2$ is propoxy; $R^3$, $R^4$, $R^5$, $R^6$, $R^7$, $R^8$, $R^9$, $R^{10}$, $R^{11}$, and $R^{12}$ are each independently hydrogen, halogen, trifluoromethyl, lower alkyl, cycloalkyl, lower alkoxy, hydroxy, nitro, cyano, —N(R$^{13}$)$_2$, phenyl, phenyloxy, benzyl or benzyloxy, or $R^6$ and $R^7$ together are a benzene ring; $R^{13}$, $R^{14}$, and $R^{15}$ are each independently hydrogen, lower alkyl or cycloalkyl, as well as their pharmaceutically acceptable salts.

21. Compounds of claim 18, wherein $R^1$ is lower alkyl or benzyl; $R^2$ is propoxy; $R^3$ is hydrogen, lower alkoxy, halogen or benzyloxy; $R^4$ is hydrogen or lower alkoxy; $R^5$ is hydrogen, halogen or lower alkoxy; $R^6$ is hydrogen; $R^7$ is hydrogen or lower alkoxy; or $R^6$ and $R^7$ taken together are a benzene ring; and $R^8$, $R^9$, $R^{10}$, $R^{11}$, and $R^{12}$ are each independently hydrogen or halogen.

* * * * *

UNITED STATES PATENT AND TRADEMARK OFFICE
CERTIFICATE OF CORRECTION

PATENT NO. : 5,958,931
DATED : September 28, 1999
INVENTOR(S) : Adam et al.

It is certified that error appears in the above-identified patent and that said Letters Patent is hereby corrected as shown below:

In claim 7, column 15, line 57, delete "(4-methoxypheny)" and insert therefor -- (4-methoxyphenyl) --.

In claim 16, column 16, line 46, delete "$R^1$-$R^{12}$" and insert therefor -- $R^1$-$R^{12}$ --.

In claim 17, column 17, line 2, delete ". . ." and insert therefor -- $_nN(R^{13}R^{14})$ or -$N(R^{15})CH_2)_nN(R^{13}R^{14})$; $R^3$, $R^4$, $R^5$, $R^6$, $R^7$, $R^8$, $R^9$, $R^{10}$, $R^{11}$ and $R^{12}$ --.

Signed and Sealed this

Twenty-seventh Day of June, 2000

Attest:

Attesting Officer

Q. TODD DICKINSON
Director of Patents and Trademarks